(12) United States Patent
Arora et al.

(10) Patent No.: US 11,755,129 B2
(45) Date of Patent: Sep. 12, 2023

(54) METHOD FOR ADAPTING SENSITIVITY OF A POINTING DEVICE, COMPUTER PROGRAM AND IMAGE EVALUATION DEVICE

(71) Applicant: KONINKLIJKE PHILIPS N.V., Eindhoven (NL)

(72) Inventors: Saurabh Arora, Bangalore (IN); Devdatt Vilas Rao Kawathekar, Bangalore (IN)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 17/619,051

(22) PCT Filed: Jul. 1, 2020

(86) PCT No.: PCT/EP2020/068434
§ 371 (c)(1),
(2) Date: Dec. 14, 2021

(87) PCT Pub. No.: WO2021/001385
PCT Pub. Date: Jan. 7, 2021

(65) Prior Publication Data
US 2022/0308681 A1    Sep. 29, 2022

(30) Foreign Application Priority Data
Jul. 2, 2019  (EP) .................... 19183751

(51) Int. Cl.
*G06F 3/038* (2013.01)
*G06F 3/0354* (2013.01)
*G06F 3/0488* (2022.01)

(52) U.S. Cl.
CPC ........ *G06F 3/0383* (2013.01); *G06F 3/03547* (2013.01); *G06F 3/0488* (2013.01)

(58) Field of Classification Search
CPC .. G06F 3/038; G06F 3/03547; G06F 3/03543; G06F 3/033; G06F 3/04812;
(Continued)

(56) References Cited

U.S. PATENT DOCUMENTS

| 5,786,805 A | 7/1998 | Barry |
| 9,910,512 B1 * | 3/2018 | Tiwary ................... G06F 3/038 |

(Continued)

FOREIGN PATENT DOCUMENTS

| EP | 3098740 A1 | 11/2016 |
| WO | 2007124614 A1 | 11/2007 |

OTHER PUBLICATIONS

International Search Report and Written Opinion for PCT/EP2020/068434; dated Sep. 2, 2020, 11 pages.

*Primary Examiner* — Koosha Sharifi-Tafreshi

(57) ABSTRACT

The invention provides a method for adapting sensitivity of a pointing device and a related image evaluation device (1). The pointing device is connected to a processor configured to execute a plurality of application workflows (A1, A2, ..., An), and to a display configured to display a cursor. The method comprises the steps of: receiving a default sensitivity (S) of the pointing device; determining one of the plurality of application workflows (A1, A2, ..., An) which is to be executed, said application workflow being the currently-active application workflow (Ai); receiving or determining a target sensitivity (Si) for the currently-active application workflow (Ai); receiving or determining a correction factor (Fi) for the currently-active application workflow based on the target sensitivity (Si) for the currently-active application workflow (Ai) and the default sensitivity (S); receiving a current position (x1,y1) of the cursor; detecting delta coordinates ($\Delta x, \Delta y$) inputted by an operation made by the user on the pointing device in order to move the cursor on the display during execution of the currently- (Continued)

active application workflow (Ai); and computing, in response to the operation of the user on the pointing device, a new position of the cursor on the display based on the current position (x1,y1) of the cursor, the delta coordinates ($\Delta$x,$\Delta$y) and the correction factor (Fi) for the currently-active application workflow (Ai).

19 Claims, 7 Drawing Sheets

(58) Field of Classification Search
CPC .. G06F 3/0383; G06F 3/0354; G06F 3/03541; G06F 3/03
USPC .................. 345/157, 163; 715/856, 857, 858
See application file for complete search history.

(56) References Cited

U.S. PATENT DOCUMENTS

| | | |
|---|---|---|
| 2004/0119682 A1 | 6/2004 | Levine et al. |
| 2007/0188458 A1 | 8/2007 | Bells et al. |
| 2007/0188459 A1* | 8/2007 | Bells ................... G06F 3/03549 345/167 |
| 2013/0088452 A1 | 4/2013 | Glaser-Seidnitzer et al. |
| 2014/0282142 A1 | 9/2014 | Lin |
| 2015/0253923 A1 | 9/2015 | Cho |
| 2016/0306491 A1 | 10/2016 | Lee et al. |
| 2018/0024647 A1 | 1/2018 | Coletrane-Pagan et al. |

* cited by examiner

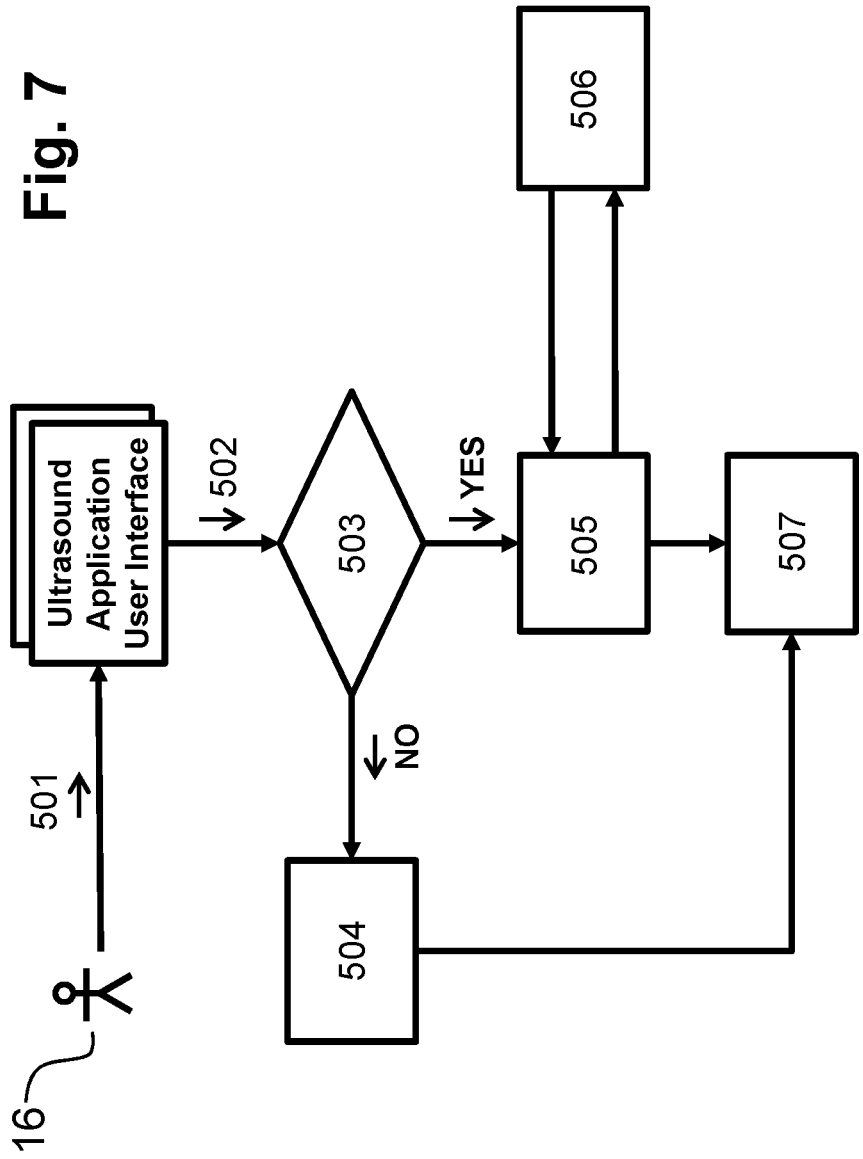

METHOD FOR ADAPTING SENSITIVITY OF A POINTING DEVICE, COMPUTER PROGRAM AND IMAGE EVALUATION DEVICE

CROSS-REFERENCE TO PRIOR APPLICATIONS

This application is the U.S. National Phase application under 35 U.S.C. § 371 of International Application No. PCT/EP2020/068434, filed on Jul. 1, 2020, which claims the benefit of European Patent Application No. 19183751, filed on Jul. 2, 2019. These applications are hereby incorporated by reference herein.

FIELD OF THE INVENTION

The present invention relates to a method for adapting sensitivity of a pointing device, a computer program and an image evaluation device configured to perform the inventive method.

BACKGROUND OF THE INVENTION

Generally, in the user interface of computer systems and also ultrasound systems, a plurality of application workflows can be executed. Usually, an application workflow includes a visualization that is displayed on a display. Further, an application workflow is usually controlled by a cursor in response to a user's operation on a pointing device. However, each application workflow has a different requirement with respect to accuracy of the movement of the curser and thus to the user's operation. In other words, there may be some application workflows that require a precise and accurate movement of the cursor, such as continuous trace measurement. On the other hand, there are other application workflows that do not need a specifically accurate movement of the cursor such as the process of hitting a button. The accuracy of the movement of the cursor mainly depends on how an operation on the pointing device is transmitted in a movement of the cursor on the display, that is, on the relationship between the operation on the pointing device and the resulting movement of the cursor on the display. For example, if the sensitivity is too high, the cursor moves very fast even for small operations on the pointing device. This may lead to inaccurate movement of the cursor on the display and, for example, to inaccurate tracing of a waveform to be measured, resulting in inaccurate measurements. Users who are not accustomed to operating the pointing device tend to make errors and need to move the cursor in the reverse direction in order to erase the incorrectly made movement and perform the movement once again. On the other hand, if the sensitivity is too low, the cursor moves very slowly even for large operations on the pointing device. Slow movements of the cursor increase the accuracy of moving the cursor on the display, however, it would lead to an increase in time taken to perform the measurement, resulting in dissatisfied user experience and overall decreased efficiency. Moreover, slow movements of the curser might also lead to an uncomfortable handling of the pointing device because the operation on the pointing device has to be relatively large, that is, if the pointing device is a touchpad, the edge of the touchpad is quickly reached.

Therefore, it would be desirable to have a solution that enables selectively controlling the sensitivity of a pointing device for different application workflows.

US 2014282142 A1 discloses a system that includes a touch screen device configurable to communicate with and control an ultrasound system. The system may further include an ultrasound user interface component configurable from the touch screen device, having one or more customizable properties, and representing an ultrasound system control component. At least one of the customizable properties of the ultrasound user interface component may be associated with a presence of the ultrasound user interface component on the touch screen device. The presence of the ultrasound user interface component on the touch screen device may be configurable via the touch screen device in response to receiving a user selection on the touch screen device.

US 2015253923 A1 discloses a method and an electronic device for detecting a user input in the electronic device. The method includes acquiring information regarding a user interface object to be displayed on a touch screen panel; setting, based on the information, a partial area that is at least a part of a touch detection area corresponding to the user interface object; and adjusting a touch detection sensitivity of the partial area to be greater than a touch detection sensitivity of the touch screen panel.

US 2016306491 A1 discloses a method and electronic device. The electronic device includes a first touch sensor and a processor. The processor implements the method, which includes detecting, via a first touch sensor of the electronic device, sensor information from a touch object, determining, via a processor of the electronic device, a state of the touch object based on analysis of the detected sensor information, and adjusting a touch sensitivity for the electronic device according to the determined state of the object.

US 2013088452 A1 discloses an electronic, context-sensitive controller system for a medical technology device, in which at least one external input and output device, with a touchscreen user interface, is provided with an adapter module. The medical technology device is operated and/or controlled via a computer-assisted application in order to exchange data with a control module. An interface between the adapter module and the control module is designed to exchange control data for control of the medical technology device via the touchscreen user interface of the external input and output device.

U.S. Pat. No. 5,786,805 A1 discloses a computer system with a graphical user interface that supports selection and dragging of graphic objects using a pointing device, that is so adapted as to provide automatic adjustment of pointing device sensitivity in a defined range on or around the object so as to create, in effect, a sticky object. By so modifying the cooperation of the pointing device and cursor, the difficult coordination required to position and then select within a narrow zone so as to invoke, for example, a dragging operation becomes simpler and more natural. It is further recognized that, by selectively blocking the modification at some predefined velocity of movement over the object, for which the attack rate by the user would not be consistent with an attempt to select an object, it is possible to avoid introducing confusing "stickiness" when no selection is intended.

US 2018/0024647 A1 discloses a computer program product including a non-transitory computer readable storage medium having program instructions embodied therewith, wherein the program instructions are executable by a processor to cause the processor to perform a method. The method includes monitoring use of a user input device of a computer system relative to a graphical user interface (GUI) of an active application, wherein the user input device includes a pointing device, wherein user input to the pointing device controls movement of a pointer within the GUI, and wherein a software interface establishes a level of sensitivity between the user input to the pointing device and the resulting movement of the pointer. The method further includes determining a value of one or more parameters characterizing the use of the at least one user input device, and automatically adjusting the level of sensitivity in response to the value of the one or more parameters.

However, the problem mentioned above remains, namely to operate a pointing device in an error-free manner for a plurality of different application workflows.

OBJECT OF THE INVENTION

It is therefore an object of the present invention to provide a method for adapting sensitivity of a pointing device, a computer program and an image evaluation device configured to perform the inventive method in which the sensitivity is adapted to a currently-active application workflow.

SUMMARY OF THE INVENTION

To better address one or more of the above-identified concerns, a first aspect of the invention provides a method for adapting sensitivity of a pointing device including the features of claim 1. Further, a second aspect of the present invention provides a computer program comprising the features of claim 13. In addition, a third aspect of the present invention provides an image evaluation device including the features of claim 14. Useful embodiments are set out in the dependent claims.

In accordance with the first aspect, the method for adapting sensitivity of a pointing device connected to a processor configured to execute a plurality of application workflows, and to a display configured to display a cursor, comprises the steps of:

receiving a default sensitivity of the pointing device;

determining one of the plurality of application workflows which is to be executed, said application workflow being the currently-active application workflow;

receiving or determining a target sensitivity for the currently-active application workflow;

receiving or determining a correction factor for the currently-active application workflow based on the target sensitivity for the currently-active application workflow and the default sensitivity;

receiving a current position of the cursor;

detecting delta coordinates inputted by an operation made by the user on the pointing device in order to move the cursor on the display during execution of the currently-active application workflow; and computing, in response to the operation of the user on the pointing device, a new position of the cursor on the display based on the current position of the cursor, the delta coordinates and the correction factor for the currently-active application workflow.

The invention advantageously allows the user e. g. a radiologist analyzing a medical image on the display to operate the pointing device with an optimal sensitivity for the currently-active application workflow. Specifically, the pointing device is used to control a movement of the cursor on the display. The display may simultaneously display a visualization of the currently-active application workflow and the cursor overlaid over the visualization. Preferably, the cursor is used to control the currently-active application workflow by moving the courser along a specific line and/or to a specific position to further execute operations e.g. to click onto a button.

An application workflow may be any type of workflow which is executed by a processor and which allows user interaction by means of cursor movement. Thus, an application workflow may be a software program, an application software, a clinical application, an operating system, or a particular workflow thereof. An application workflow may be any application software requiring user interaction, such as a text or image processing application, an email application, a browser etc. For example, an application workflow may be a part of an image evaluation software program, wherein a user is required to evaluate an image by marking or tracing certain features on an image displayed on a display. According to a further example, an application workflow may be a part of a software program wherein a user may select options on a graphical user interface, e.g. by clicking on buttons or actuating drop-down menus, sliders etc. Further, an application workflow may be a workflow used to control a medical imaging device or a medical image evaluation device, such as an ultrasound system. In useful embodiment, an application workflow is executed within a particular window on the display.

The display may be any device allowing the display of images and other graphical elements, such as cursors. In particular, the display is a graphical display such as a screen, a monitor, a touch-screen, or a silver screen displaying optically projected images. In some embodiments, the display is or is part of a computer monitor, television set, tablet computer, smartphone, handheld device or the like.

The cursor may be any element which can be displayed on a display and which is preferably used in some way to operate an application workflow, e.g. a marker, a measurement cursor, an annotation or an arrow. In useful embodiments, the cursor is a graphical element overlaid on an image or a visualization and indicating a particular point or pixel on the display. The cursor may e. g. take the shape of an arrow, circle, diamond, crosslines or combinations thereof, which indicate a particular point or pixel on the display, e. g. by the center of the crosslines being positioned at that particular pixel of the display. Often, the cursor is displayed in a contrasting color to the background image or visualization, e. g. in white, yellow or black. Alternatively, the cursor may be displayed transparently, so as not to obscure the underlying image on which it is overlaid.

The pointing device may be any device which allows a user to move a cursor on a display. For example, the pointing device may be a touchpad, a joystick, a mouse, a trackball etc. In some embodiments, the user may choose a specific pointing device depending on her or his proclivity.

The connection between the pointing device and the processor may be established such that both members can communicate with each other, that is, each of the members may send electrical signals to the other one. This connection may be established by a physical connection (e.g. by a cable) or by a wireless connection (e.g. via Near Field Connection, Bluetooth connection, etc.). Similarly, the display may be connected to the processor by a physical connection or by a wireless connection. The plurality of application workflows may inter alia include tracing a displayed contour, i.e. continuous trace measurement, scrolling through a plurality of images, clicking a button on the display and so on. Specifically, the application workflows may be used to analyze images and/or corresponding information in order to carry out a measurement procedure.

Generally, a sensitivity of a pointing device may be a multiplier to transform a detected operation on the pointing device into a cursor movement on the display. In other words, if the detected operation on the pointing device (e.g. movement of the pointing device) is expressed by changes in a x- and y-direction of an ordinary coordinate system and is $\Delta x$ and $\Delta y$, a new cursor position $x_{new}$ and $y_{new}$ may be determined by $x_{new}=x_1+S*\Delta x$ and $y_{new}=y_1+S*\Delta y$, wherein $x_1$ and $y_1$ indicate the current position of the cursor on the display. As a result, a distance issued by the operation on the pointing device by a user and a distance covered by the cursor on the display may differ from each other. Specifically, the distance covered by the cursor may be larger as compared to the distance issued by the user by operating the pointing device. This provides the advantage that less space is required for operating the pointing device while at the same time a larger distance on the display may be covered by the cursor. The distance issued by the operation on the pointing device by the user may be, for example, in case the pointing device is a touchpad, the distance that is covered by an index finger of the user on the touchpad.

The default sensitivity may be dependent on the pointing device that is used. In an embodiment, the default sensitivity is stored within the pointing device and is transmitted to the processer before an application workflow is executed. Alternatively, the default sensitivity for one or more pointing devices may be stored in another storage connected to the processor. That is, different pointing devices may be used with the same processor. Therefore, the user may use a plurality of different pointing devices, wherein the operation of the application workflow that is executed is the same for each pointing device.

Before an application workflow is started, the user may select one of the plurality of application workflows. This may be done by using the pointing device or by using another user interface. The selected application workflow will then be executed by the processor and is defined as the currently-active application workflow. Alternatively, the processor may automatically set an application workflow based on a specific pointing device connected to the processor and/or based on a further device connected to the processor, for example, an ultrasound probe.

The target sensitivity represents a desired sensitivity for the currently-active application workflow. That is, there may be a different target sensitivity for each of the plurality of application workflows. The target sensitivity may be defined in advance. Specifically, the target sensitivity may be based on field studies and/or tests in which it is investigated which sensitivity is the best for a specific application workflow. In other words, it is tested which sensitivity promises the most successful operations on the pointing device controlling the respective application workflow.

The target sensitivity may be received based on the application workflow that was previously selected by the user or set by the system. Subsequently, the correction factor is determined based on the default sensitivity and the target sensitivity. As a result, the sensitivity may be adapted to both the pointing device (i.e. by the default sensitivity) and to the specific application workflow that is executed (i.e. by the target sensitivity).

Alternatively, the target sensitivity may be determined based on the correction factor and the default sensitivity. The correction factor may be manually inputted by the user via a user interface or may be stored in a storage in advance and may be selected by the user or automatically by the processor. Preferably, the correction factor has been determined previously (e.g. by a previous cycle of the inventive method) and is stored in a storage connected to the processor, wherein the stored correction factor may include information of the specific user that has operated the pointing device.

Thus, the target sensitivity is received (preferably based on the currently-active application workflow) or is determined (preferably based on the default sensitivity and the correction factor). Whether the target sensitivity is received or determined depends preferably on whether a handover variable is used in order to provide information of a previously use of the application workflow by the user or not. In other words, in order to provide a specific profile of the user controlling the currently-active application workflow via the pointing device, information from a previous process of controlling said currently-active application workflow are handed over to a currently-active application workflow. In some embodiments, the handover variable may be the correction factor. In this case, the target sensitivity may be determined. As a result, due to the variability of determining or receiving the target sensitivity, the method is applicable in cases in which the user operates the pointing device in order to control the currently-active application workflow for the first time or in cases in which the user has a pointing device navigation history.

The correction factor may represent a factor that may be used to adapt the values of $\Delta x$ and $\Delta y$ described above. That is, the correction factor may increase or decrease the values of the detected delta coordinates. The correction factor may be defined for each application workflow separately and the factor may be determined heuristically based on an expected usage pattern of the pointing device in the currently-active application workflow. In an embodiment, the correction factor for the currently-active application workflow may be a ratio of the target sensitivity for the currently-active application workflow and the default sensitivity.

Preferably, the current position of the cursor, i.e. the position on the display thereof, is represented by x and y values. The position may be also represented by pixels in a first specific direction of an arbitrary coordinate system and by pixels in a second direction of the arbitrary coordinate system perpendicular to the first direction. The current position of the cursor may be also received by loading the previously determined and stored new position of the cursor computed by a previous cycle of the inventive method.

Advantageously, the delta coordinates may be relative coordinates. Further, the delta coordinates may be inputted by the user's operation on the pointing device. In other words, the delta coordinates are issued by the pointing device in response to an operation of the user thereon. For example, if the user moves the pointing device such as a mouse, there is a relative distance detected by the pointing device. Subsequently, the distance may be divided into coordinates. These coordinates may represent the delta coordinates.

Preferably, the new cursor position may be computed by adding the updated delta coordinates (updated by multiplying with the correction factor) to the previous cursor position.

Advantageously, an effect can be achieved that movements of the cursor on the display may be controlled by reducing or increasing raw pointing device movements within the currently-active application workflow where sensitivity needs to be controlled.

The invention thus provides a method and a related device to selectively control the sensitivity of a pointing device for different application workflows. It provides the advantage that each of a plurality of application workflows each requiring a different pointing device sensitivity may be efficiently executed on one single device.

In a useful embodiment, the correction factor for the currently-active application workflow is a ratio of the target sensitivity for the currently-active application workflow and the default sensitivity. In other words, the correction factor may be determined by dividing the target sensitivity by the default sensitivity.

According to a useful embodiment, the pointing device may be a touchpad configured to receive a touch gesture based on the user's operation on the touchpad. Particularly, a touchpad or trackpad may be a pointing device featuring a tactile sensor having a specialized surface that can translate the motion and position of a user's fingers to a relative position, that is, to the delta coordinates described above. For example, a touch gesture may be a zoom-in function by using two fingers approaching each other or a zoom-out function by using two fingers moving away from each other. Further, tapping with one finger onto the touchpad may refer to a left mouse click on a conventional computer mouse, tapping with two fingers onto the touchpad may refer to a right mouse click on a conventional computer mouse etc. Advantageously, touchpad devices may be capable of supporting various modern features like gestures which conventional trackball does not support. Further, several usability studies for ultrasound system suggest that navigation on a touchpad is much more sensitive compared to trackball in several ultrasound workflows. However, this creates a challenge to users to perform error-free actions (e.g. continuous trace measurements) while using a touchpad. Specifically, users expect controlled sensitivity of touchpad in certain application workflows. For example, in continuous trace measurement workflow, user may move his/her index finger across the touchpad in a specific direction so that the cursor closely follows the waveform (i.e. a contour).

In a useful embodiment, for each application workflow of the plurality of application workflows there may be defined a corresponding target sensitivity. Specifically, there may be needed different sensitivities of the pointing device for different application workflows. For example, in an application workflow in which a movement of the cursor is controlled in order to select a specific button such as system setups: In this case the area covered by the button in the user interface, i.e. on the display, is usually high, and it is acceptable if the cursor is present at any place within the area covered by the button. Therefore, accuracy is not a big concern in this case and hence the user wants the cursor movement to be fast, requiring a higher pointing device sensitivity (e.g. S=1 or closer). On the other hand, in case a movement of the cursor using the pointing device is controlled in order to closely trace a waveform or an anatomical boundary in an ultrasound image, e.g. in order to perform a measurement, the user must accurately move the cursor on an underlying image of the waveform or anatomy. This requires the user to move the cursor at a controlled (slightly slower) speed, requiring lower pointing device sensitivity (e.g. S=0.4 to S=0.75). According to the present embodiment, these concerns are addressed. As a result, an optimal adaption of the sensitivity of the pointing device to the respective application workflow (depending on whether the currently-active application workflow requires an accurate control of the movement of the cursor or not) may be provided.

According to a further useful embodiment, the correction factor for the currently-active application workflow is automatically adapted based on the user's pointing device navigation history for said application workflow, preferably based on the user's last use of the pointing device for said application workflow. Specifically, the navigation history may include information of how accurate the movement of the cursor was the last time, when the user did execute the currently-active application workflow. Further, automatically may mean that the correction factor is adapted every time when new delta coordinates are detected. Alternatively, the correction factor may be updated in a pre-set time interval, preferably every 0.01 s to 1 s, most preferably every 0.1 to 0.5 s.

Moreover, different users may have different skills with respect to operating the pointing device. That is, some skilled user may operate the pointing device while executing a specific application workflow with a relatively high sensitivity while other users struggle to operate the pointing device at this specific sensitivity.

According to a preferred embodiment, the method may comprise the steps of: determining a number of erroneous operations made by the user on the pointing device, wherein an operation is defined to be erroneous when the user causes the cursor to move in a reverse direction in order to undo a previously made move operation of the cursor; determining a number of successful operations made by the user on the pointing device, wherein an operation is defined to be successful when the user causes the cursor to move in a forward direction in order to perform a further forward move operation of the cursor; and adapting the correction factor for the currently-active application workflow based on the determined number of erroneous operations and successful operations. In other words, a user operation on the pointing device to move the cursor in a reverse direction to 'undo' a trace he/she has drawn may be recorded as an error event for the purpose of machine learning, wherein machine learning may mean that the number of erroneous operations and successful operations made by a specific user in one specific application workflow is recorded and further used in order to adapt the correction factor for the currently-active application workflow. Similarly, a user action to move the cursor in a forward direction to 'perform' the trace is recorded as a success event (i.e. successful operation) for the purpose of machine learning. As a result, a machine learning algorithm for auto-adapting touchpad sensitivity based on user's past usage of the touchpad may be provided. That is, the correction factor based on the user's touchpad navigation history may be automatically adapted. Thereby, of user-specific set of correction factors for one or several application workflows may be created. Further, an individualized sensitivity depending on the respective skill level of the user for the currently-active application workflow may be provided. The method steps of this embodiment may be carried out prior to the computing step, and preferably they are repeated at pre-determined intervals during execution of the currently-active application workflow.

In a useful embodiment, the correction factor for the currently-active application workflow is adapted by subtracting a scale down factor multiplied by the correction factor from the correction factor, if the number of erroneous operations exceeds a predefined first threshold value and if the movement of the cursor in the forward direction due to the operation of the user is within a predefined window limit of move points, or the correction factor for the currently-active application workflow is adapted by adding a scale up factor multiplied by the correction factor to the correction factor, if the number of successful touch gestures exceeds a predefined second threshold value. Specifically, the display may be subdivided in a plurality of pixels. Further, the window limit may describe a number of pixels that are covered or crossed by the cursor. In addition, the forward direction is defined, for example from a left side of the display to the right side thereof or vice versa, depending on the currently-active application workflow. That is, forward direction may be the working direction e.g. the direction in which a contour displayed on the display is traced. Particularly, the number of pixels may be counted such that only pixels are added to the number of pixels covered by the cursor in the forward direction. Moreover, the direction which is defined to be the forward direction may be set by the respective application workflow that is executed. The window limit may be set to a value between 50 and 1000 pixels, preferably to a value between 50 and 150 pixels, most preferably to a value around 100 pixels. If the number of error events NumErrorEvents exceeds a certain number MaxErrorsLimit, the algorithm (i.e. the method) assumes that the sensitivity is too high for the current user and currently-active application workflow and hence changes the correction factor for that currently-active application workflow using a scale down factor ScaleDownFactor. A check is made to not reduce the correction factor $F_i$ below a certain minimum limit of the scale down factor defined as $F_i$Min. In other words, the following relations are applied:

If NumErrorEvents>MaxErrorsLimit $F_i=F_i-F_i*$ScaleDownFactor

If $F_i<F_i$Min, set $F_i=F_i$Min

Further, if the number of success events NumSuccessEvents exceed a certain number MinSuccessEventsLimit, the algorithm (i.e. the method) assumes that pointing device sensitivity is good for performing the measurement accurately and it can increase the sensitivity a little to speed up the measurement operation. The correction factor for that application is changed using a scale up factor ScaleUpFactor. A check is made to not increase the correction factor beyond a certain maximum limit defined as $F_i$Max. In other words, the following relations are applied:

If NumSuccessEvents>MinSuccessEventsLimit $F_i=F_i+F_i*$ScaleupFactor

If $F_i>F_i$Max, set $F_i=F_i$Max

The limits and scaling factors stated above may be determined by performing an experimental data collection on touchpad usage by a diverse set of users on different applications workflows. Further, the implementation of restrictions (i.e. the window frame, the scale up limit and the scale down limit) may provide the possibility to set boundaries in order to avoid excessive increase or decrease of the respective values.

According to a useful embodiment, the correction factor for the currently-active application workflow may be adapted by subtracting a scale down factor multiplied by the correction factor from the correction factor, if the number of erroneous operations exceeds a predefined first threshold value within a predefined period of time, or the correction factor for the currently-active application workflow may be adapted by adding a scale up factor multiplied by the correction factor to the correction factor, if the number of successful operations exceeds a predefined second threshold value. In this preferred embodiment the same aspects may be applicable as mentioned in connection with the before described embodiment with the exception that there is no window limit as requirement for adapting the correction factor but a time limit. In other words, the correction factor may be adapted by the scale down factor in case the predefined number of erroneous operations is reached within a time limit. If the operation is performed during the specified time limit without reaching the predefined number of erroneous operations, the correction factor is not adapted. Similarly, if predefined number of erroneous operations is reached but the specified time limit has not elapsed, the correction factor is not adapted. This may provide a facilitated configuration because there is no counting of pixels necessary. Further, the process may be independent from a resolution of the display (i.e. the number of pixels provided on the display). Moreover, it may be easier to adjust the method to new hardware, for example, by changing the period of time (pixel adaption might be complex due to different amount of pixels provided in different displays).

According to a further useful embodiment, for each application workflow of the plurality of application workflows there may be defined a corresponding predefined first and/or second threshold value. Thereby, the sensitivity of the pointing device may be more or less susceptible to be auto-adapted by the user's navigation history in different application workflows. For example, a clinical application workflow may have lower thresholds than an application workflow where the user only has to press one of a number of buttons.

In a useful embodiment, the target sensitivity for at least one application workflow of the plurality of application workflows may be adapted by the user via a user interface. In other words, the user may directly influence the sensitivity—e.g. the sensitivity of the currently-active application workflow—so as to individually adapt the sensitivity (e.g. when the user's needs are not met by the automatic adaption). The target sensitivity may be inputted via the user interface. More preferred, the user may increase or decrease the sensitivity via the user interface, e.g. by actuating a scroll bar, slider or mouse wheel. As a result, the user may individually judge in which situations the highest sensitivity should be applied and in which situations this is not necessary (e.g. when optimal measurement results are not necessary, for training purposes etc.). That is, there may be a possibility to intervene for the user.

In a further useful embodiment, when the currently-active application workflow is terminated, the adapted correction factor is saved within a storage connected to the processor. The storage may be an internal storage that is provided in the same system as the processor or may be an external storage connected to the processor. The correction factor is saved with corresponding information relating to the user (e.g. user id, personal number etc.) and to the respective application workflow. When the user performs the same application workflow next time, the computation of the new position of the cursor may be based on the previously saved correction factor. Advantageously, the user may increase his/her skills from one time to another and therefore the efficiency of working. Further, better training for new unskilled/new personal may be provided and the user's skill may be monitored.

According to a useful embodiment, the method may comprise the steps of: setting the correction factor for the currently-active application workflow to a predefined maximum correction factor if said correction factor exceeds a predefined maximum correction factor; or setting the correction factor for the currently-active application workflow to a predefined minimum correction factor if said correction factor falls below a predefined minimum correction factor. This applies in particular to these embodiments in which the sensitivity is automatically adapted based on the user's last use of the pointing device, or in which it can be adapted by the user. Therefore, an excessively high sensitivity and thus potential impreciseness while executing a measurement may be avoided. Further, minimum standards may be defined and set in advance. Preferably, such steps are carried out prior to the computing step.

The invention is also related to a computer program comprising program code instructions which, when executed by a processor connected to a display, enables the processor to carry out the above-defined method in particular the inventive method in one of its embodiments. Such a computer program may be written in any code, as it requires mostly manipulation of elements displayed on a display. The processor executing the method may be any kind of calculation device including a graphics card or graphics processing unit (GPU), a central processing unit (CPU), chip or other processing device. The processor may be part of a computer such as general-purpose computer, PC, workstation, control console of a medical image device, in particular an ultrasound scanner, a server or a cloud computer. The processor will in useful embodiments be part of an imaging modality such as an ultrasound, MR or CT scanner. Alternatively, the method may be executed on a standalone device configured for image analysis, which is not used to control an image capturing device.

Further, the above-defined computer program may be provided on a computer-readable medium. The computer-readable medium may be any digital data storage device, such as a USB-stick, CD-ROM, SD-card, SSD-card, Hard disc etc. Naturally, the computer program need not to be stored on such a computer-readable medium to be supplied to customers, but may be downloaded from a distant server or cloud, e.g. over the internet.

The invention is also directed to an image evaluation device configured to execute a plurality of application workflows and to perform an embodiment of the inventive method. Such image evaluation device comprises a display configured to display an image for evaluation and a cursor and a pointing device configured to detect delta coordinates of an operation made by a user on the pointing device in order to perform a move operation of the cursor on the display. Further, the image evaluation device comprises a processor—as described above—configured to receive a default sensitivity of the pointing device, to determine one of the plurality of application workflows which is to be executed, said application workflow being the currently-active application workflow, to receive or determine a target sensitivity for the currently-active application workflow, to receive or determine a correction factor for the currently-active application workflow based on the target sensitivity for the currently-active application workflow and the default sensitivity and to compute, in response to the operation of the user on the pointing device, a position of a cursor in a display based on a current position of the cursor, the delta coordinates, and the correction factor for the currently-active application workflow.

In useful embodiments, the image evaluation device may be an ultrasound system, and the pointing device may be a touchpad configured to receive a touch gesture based on the user's operation on the touchpad. Specifically, in newer generation ultrasound systems a touchpad is implemented as the pointing device as touchpad devices may be capable of supporting various modern features like gestures which conventional trackball does not support. However, several usability studies for ultrasound system suggests that navigation on a touchpad is much more sensitive compared to a trackball in several ultrasound workflows.

According to an embodiment, the correction factor ($F_i$) for the currently-active application workflow is a ratio of the target sensitivity ($S_i$) for the currently-active application workflow and the default sensitivity (S).

Any feature or useful embodiments described in connection with the inventive method also apply to the image evaluation device.

BRIEF DESCRIPTION OF THE DRAWINGS

The invention shall now be illustrated by means of particular embodiments with reference to the attached drawings, in which:

FIG. 7 is a flow chart illustrating a method according to an embodiment of the present invention.

DESCRIPTION OF EMBODIMENTS

Throughout the figures, the same or corresponding features/elements of the various embodiments are designated with the same reference signs.

Figure 1:
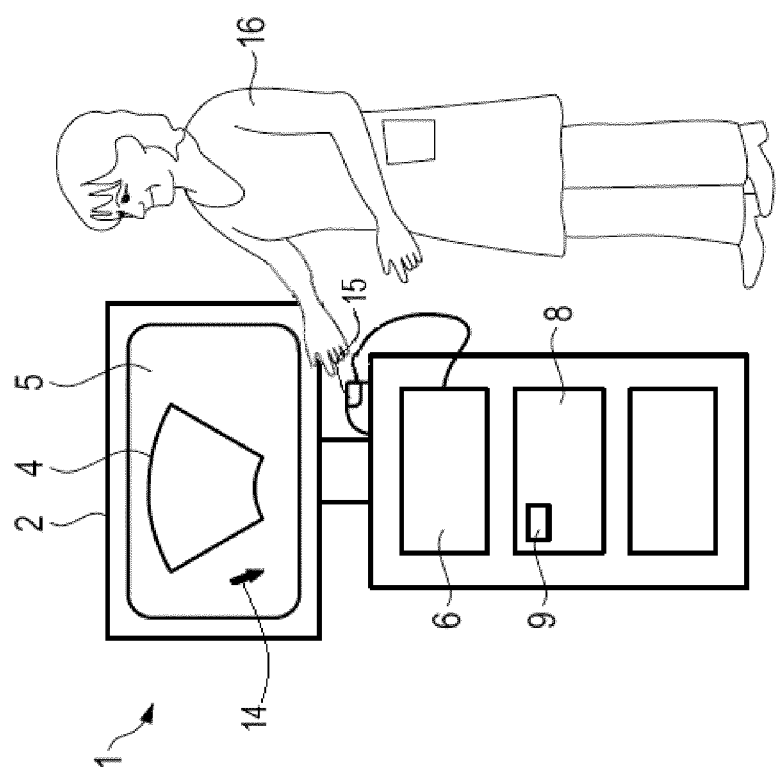
FIG. 1 shows schematically an image evaluation device according to an embodiment of the present invention.

FIG. 1 schematically illustrates an imagining evaluation device 1 for executing a plurality of application workflows $A_1, A_2, \ldots, A_n$, which in this case is part of an ultrasound imagining machine or ultrasound scanner. The image evaluation device 1 includes a computer screen 2 having a display 5. A medical image (specifically an ultrasound image) 4 and corresponding information are currently displayed on the display 5. A pointing device 15 such as a touchpad, a computer mouse, a trackball etc. is provided for controlling a movement of a cursor 14 on the display 5. The cursor 14 is displayed on the display 5 so as to be overlaid over the further displayed elements, i.e. such that the cursor 14 can be moved over the displayed elements.

The image evaluation device 1 further includes a processor 6, such as a CPU and/or a graphics card, which is able to control any images or elements displayed on the display 5. The processor 6 is configured to execute an embodiment of the inventive method. The image evaluation device 1 further includes a data storage medium 8, such as a hard disc, on which a computer program necessary for executing the invention on the image evaluation device 1 or its processor may be stored. Further, there may be an insertable computer-readable medium 9, e.g. USB-stick, which may be used to load the necessary computer program onto the image evaluation device.

The image evaluation device 1 can be operated by a user 16. The user 16 may be any person who wishes to perform an accurate image evaluation and thus executes the application workflow $A_1, A_2, \ldots, A_n$. In case of medical images to be evaluated, the user 16 will often be a radiologist or radiographer, but can also be a specialist in any other field, such as gynaecologist, a cardiologist etc. An embodiment of the invention provides a method to selectively control the sensitivity of the pointing device 15 for different application workflows $A_1, A_2, \ldots, A_n$.

Figure 2:
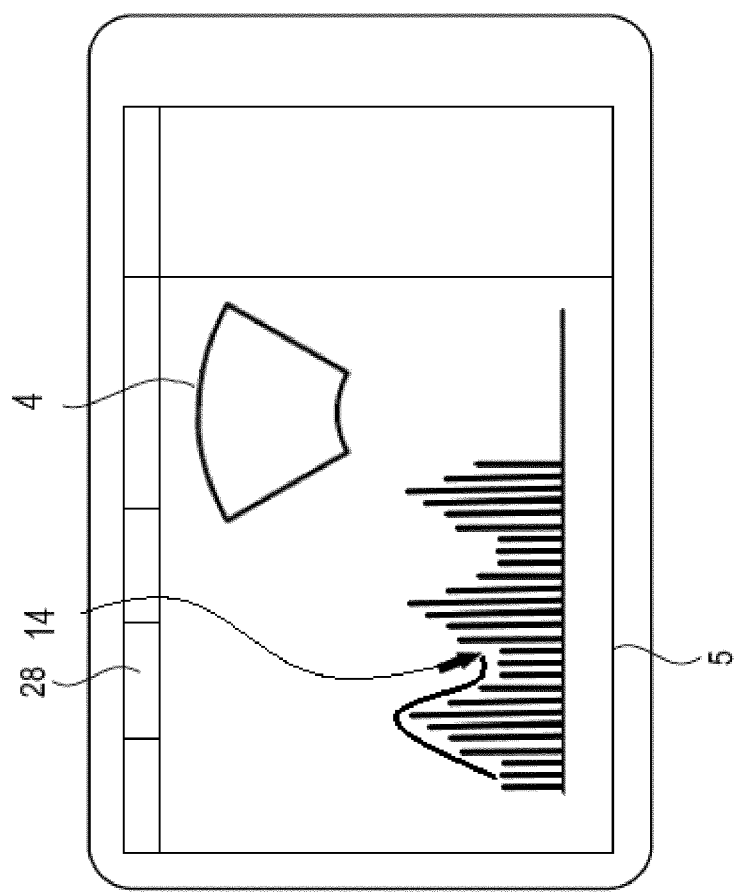
FIG. 2 shows schematically a display of the image evaluation device of FIG. 1 on which a currently-active application workflow is executed.

FIG. 2 provides a front view of the display 5 while a continuous trace measurement is executed as one of the plurality of application workflows $A_1, A_2, \ldots, A_n$. That is, the continuous trace measurement is the currently-active application workflow $A_i$. In the continuous trace measurement, the user 16 has to draw a trace along an outline of a contour (e.g. a waveform) representing information relating to the ultrasound image 4 which is displayed, too. The trace is drawn on the display 5 using the cursor 14. Therefore, the user has to operate the pointing device 15 such that the cursor 14 accurately moves along the contour in order to align the trace as close as possible to the contour. Consequently, a correct measurement can be executed afterwards. In order to move the cursor 14 on the display 5 the user 16 operates the pointing device 15. In more detail, using the pointing device 15, the user 16 moves (in case of a computer mouse), tilts (in case of an joy stick), rotates (in case of a track ball) or inputs a gesture (in case of a touchpad) in order to operate the pointing device 15. Regardless which device is implemented as the pointing device 15, delta coordinates $\Delta x, \Delta y$ are detected by the pointing device 15 based on the operation of the user 16 on the pointing device 15.

Generally, in order to transmit delta coordinates $\Delta x, \Delta y$ detected based on the operation of the user 16 on the pointing device 15 into a movement of the cursor 14 on the display 5, a sensitivity is used as a factor in order to adapt the delta coordinates $\Delta x, \Delta y$. In other words, the sensitivity influences the conversion of the operation on the pointing device 15 into the movement of the cursor 14 on the display 5. For example, if the sensitivity is high, a small amount of operation on the pointing device 15 results in a large movement of the cursor 14 on the display 5. On the other hand, if the sensitivity is low, a big amount of operation on the pointing device 15 results in a small movement of the cursor 14 on the display 5. Each pointing device 15 has its own sensitivity dependent on its structural configuration. This sensitivity is referred to as default sensitivity S. Further, the default sensitivity S may be adjusted by the operation system of the processor 6 to which the pointing device 15 is connected. Moreover, the default sensitivity S may be additionally adjusted by the user 16.

Each of the above mentioned application workflows $A_1, A_2, \ldots, A_n$ has its own optimal sensitivity. In other words, each of the application workflows $A_1, A_2, \ldots, A_n$ such as continuous trace measurement, scrolling through a plurality of images, clicking onto a button on the display 5, etc., deals with other procedures and has thus its own demand with respect to accuracy. Consequently, it is neither applicable nor sufficient to perform all application workflows $A_1, A_2, \ldots, A_n$ with the same sensitivity. Therefore, each application workflow has its own target sensitivity $S_1$ which represents a sensitivity that is the best for the specific application workflow $A_1, A_2, \ldots, A_n$. The target sensitivity $S_1$ for each application workflow $A_1, A2, \ldots, A_n$ is determined in advance, for example by field studies or other tests of the user behaviour with respect to a specific application workflow $A_1, A_2, \ldots, A_n$.

According to present invention, the delta coordinates $\Delta x, \Delta y$ detected as described above, the default sensitivity S and the target sensitivity $S_i$ are used by the processor 5 to compute a new position $x_{NEW}, y_{NEW}$ of the cursor 14 on the display 5. In other words, the sensitivity (i.e. the transmission of the operation on the pointing device 15 and the resulting movement of the cursor on the display 5) is influenced by both the default sensitivity S and the target sensitivity $S_1$ for a currently-active application workflow.

Further, a control bar 28 on the top of the display 5 is provided to accommodate further user input, for example by means of drop-down menus allowing the user to select a specific image and/or corresponding information to be analyzed, as well as further selections.

In the following, the inventive method will be described in more detail with reference to FIGS. 3 to 7.

Figure 3:
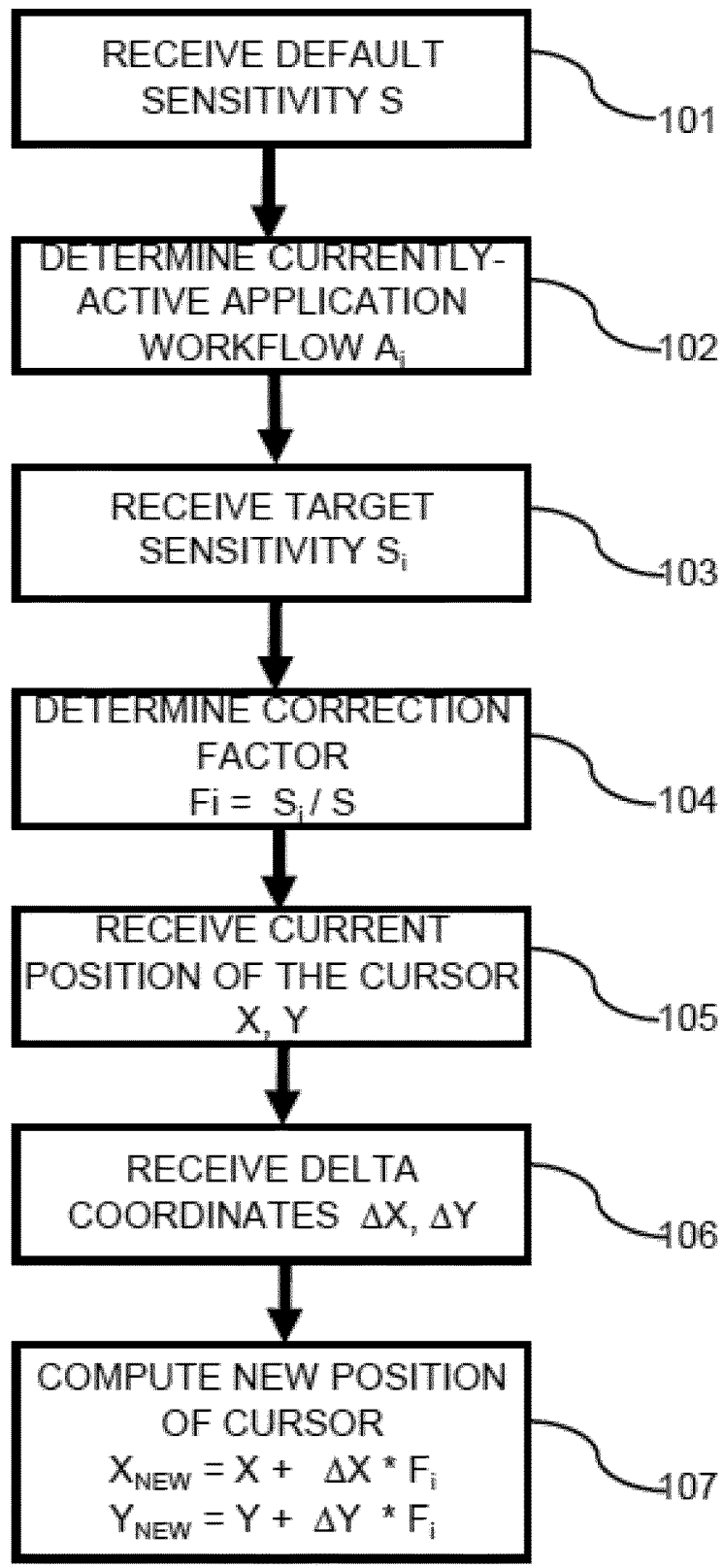
FIG. 3 is a flow chart illustrating a method according to an embodiment of the present invention.

FIG. 3 shows a flow chart of the method for adapting sensitivity of a pointing device according to an embodiment of the present invention. The method can be executed by the above described image evaluation device 1.

In step 101, the default sensitivity S is received. In the present embodiment, the pointing device 15 is a touchpad, therefore, the default sensitivity S received in step 101 describes the relationship between the distance moved with the finger on the touchpad and the distance the cursor 14 moves on the display 5.

Subsequently, in step 102 one application workflow out of the plurality of application workflows $A_1, A_2, \ldots, A_n$ is determined and defined as the currently-active application workflow $A_i$. In the present embodiment the currently-active application workflow $A_i$ is the continuous trace measurement (refer to FIG. 2).

Then, in step 103 the target sensitivity $S_i$ based on the currently-active application workflow $A_i$ is received. In one embodiment, the target sensitivity $S_i$ for each of the application workflows $A_1, A_2, \ldots, A_n$ is loaded from the storage medium 8. In that case in which there is no target sensitivity $S_i$ stored for the specific currently-active application workflow $A_i$, the user 16 may manually input a new target sensitivity $S_i$ for the currently-active application workflow $A_i$ and store it within the storage medium 8. In another embodiment, the user 16 may define that the target sensitivity $S_i$ for the currently-active application workflow $A_i$ should correspond to the default sensitivity S.

In the next step 104 the correction factor $F_i$ for the currently-active application workflow $A_i$ is determined based on the target sensitivity $S_i$ for the currently-active application workflow $A_i$ and the default sensitivity S. Specifically, the correction factor $F_i$ may be the target sensitivity $S_i$ divided by the default sensitivity.

Subsequently, in step 105, the current position $x_1, y_1$ of the cursor 14 on the display 5 is received. In some embodiments, in case the cursor 14 was not moved, the current position $x_1, y_1$ corresponds to a default position. In one embodiment, the default position is in the middle of the display to facilitate the discoverability of the cursor 14 on the display 5.

In step 106, the delta coordinates $\Delta x$ and $\Delta y$ are received. The delta coordinates are based on the operation of the user 16 on the pointing device 15. In one embodiment, the pointing device 15 is a touchpad. As a result, the delta coordinates $\Delta x, \Delta y$ correspond to a relative movement of a finger of the user 16 on the touchpad.

Subsequently, in step 107, the new position of the cursor 14 on the display 5 is computed based on the current position $x_1, y_1$ of the cursor 14, the delta coordinates $\Delta x, \Delta y$ and the correction factor $F_i$ for the currently-active application workflow $A_i$ ($x_{NEW}=x+\Delta x*F_i$ and $y_{NEW}=y+\Delta y*F_i$).

Finally, the move operation of the cursor 14 is performed so as to move the cursor 14 on the display from the current position $x_1, y_1$, to the new position $x_{new}, y_{new}$.

The following commented code provided for illustrative purpose only may be used, in part, for the above described method according to one embodiment of the present invention:

```
void Move (const Spoint& pt)
{
    // SPoint is a structure to hold x and y coordinates
    SPoint newPt;
    newPt = GetActivePoint( ); // Helper function to get the current active point
    SPoint tempPoint = pt;
    // Sensitivity Adjustment Factor (Fi) =
    // Desired Sensitivity (Si) / Current Sensitivity (S)
    tempPoint.x = pt.x * Fi;
    tempPoint.y = pt.y * Fi;
    newPt = tempoint + GetActivePoint( );
    // Perform final move operation with the newly calculated
    // point, after applying sensitivity Adjustment Factor (Fi)
    PerformFinalMove (newPt);
}
```

Figure 4:
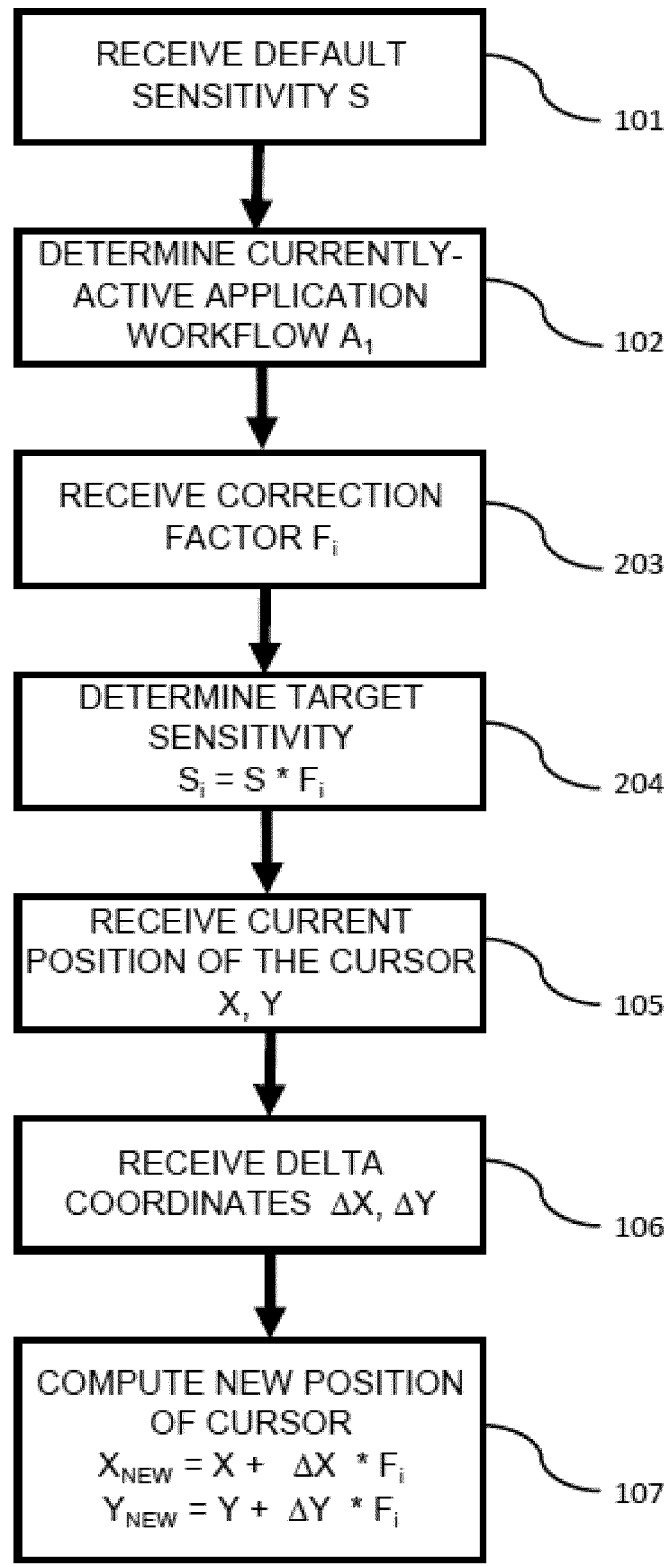
FIG. 4 is a flow chart illustrating a method according to an embodiment of the present invention.

FIG. 4 shows a flow chart of the method for adapting sensitivity of a pointing device according to another embodiment of the present invention. The method can be executed by the above described image evaluation device 1.

The method illustrated in FIG. 4 differs from that one in FIG. 3 in that the steps 103 and 104 are replaced by the steps 203 and 204 the further method steps correspond to the above described. Therefore, in the following, only the steps 203 and 204 are described with reference to FIG. 4.

In step 203, the correction factor $F_i$ is received. In one embodiment, the correction factor $F_i$ is stored within the storage medium 8.

In step 204 the target sensitivity $S_i$ is determined based on the default sensitivity S and the correction factor $F_i$. Specifically, the target sensitivity $S_i$ is determined by multiplying the default sensitivity S with the correction factor $F_i$ ($S_i = S*F_i$). However, the step 204 is not necessary for computing the new position of the cursor 14 on the display. In some embodiments, the sensitivity $S_i$ determined in step 204 is used for information purpose and/or to provide a possibility for the user 16 to intervene in that the user 16 may directly change the target sensitivity $S_i$ and cause the method to proceed to step 104.

In the following, further embodiments of the present invention will be described with reference to FIG. 5.

Figure 5:
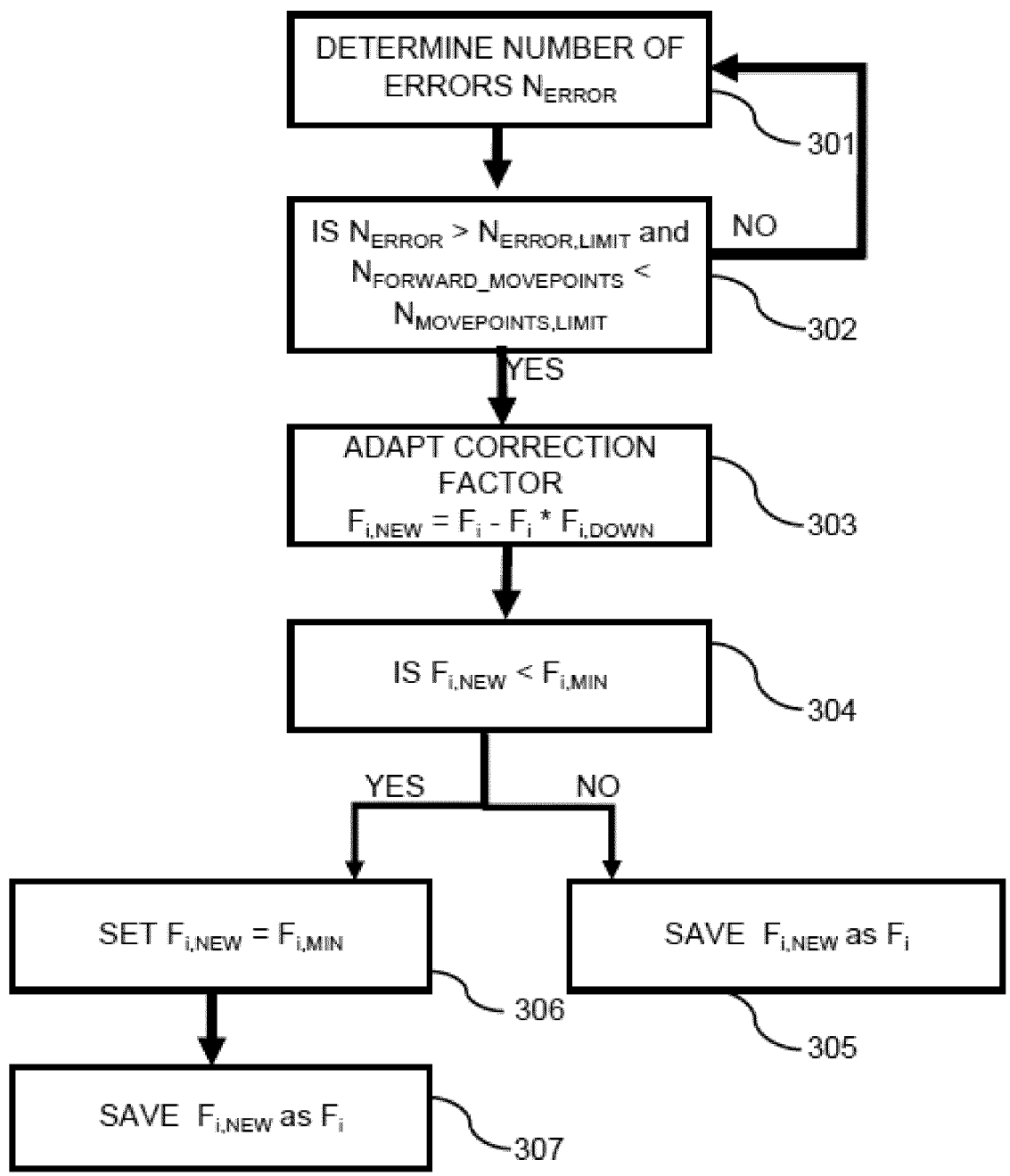
FIG. 5 is a flow chart illustrating a method according to an embodiment of the present invention.

FIG. 5 is a flow chart illustrating a method according to the present invention. Specifically, the method provides an automatically adaption of the correction factor based on the user's pointing device 15 history. The method illustrated in FIG. 5 is executed before the computing step 107 (see FIGS. 3 and 4). Particularly, in some embodiments the method is executed between steps 106 and 107, however, there are some other embodiments in which the method is executed between the steps 104 and 105 with respect to FIG. 4 and between steps 203 and 204 or 105 with respect to FIG. 4.

In step 301, the number of errors $N_{ERROR}$ is determined. Specifically, each error made by the user 16 while executing the currently-active application workflow $A_i$ is accumulated. The number of errors $N_{ERROR}$ is temporarily stored within the storage medium 8.

Subsequently, in step 302, it is determined whether the number of errors $N_{ERROR}$ exceeds a limit of numbers of errors $N_{ERROR,LIMIT}$ or not, and whether a number of forward move points $N_{FORWARD,MOVEPOINTS}$ exceeds a preset number of forward move points $N_{MOVEPOINTS,LIMIT}$ or not. If both conditions are fulfilled (YES in step 302) the process proceeds to step 303. Otherwise (NO in step 302) the process returns to step 301.

In step 303, the correction factor $F_i$ is adapted in that the a new correction factor $F_{i,NEW}$ is determined based on the current correction factor $F_i$ and a scale down correction factor $F_{i,DOWN}$. Specifically, the new correction factor $F_{i,NEW}$ is determined by subtracting the product of the current correction factor $F_i$ and the scale down correction factor $F_{i,DOWN}$ from the current correction factor $F_i$ ($F_{i,NEW} = F_i - F_i * F_{i,DOWN}$).

In step 304 it is determined whether the new correction factor $F_{i,NEW}$ is less than a preset minimum limit correction factor $F_{i,MIN}$ which represents a minimum permissible value. In case the new correction factor $F_{i,NEW}$ is less than the minimum limit correction factor $F_{i,MIN}$ (YES in step 304), the process proceeds to step 306. Otherwise, in case the new correction factor $F_{i,NEW}$ is bigger than the minimum limit correction factor $F_{i,MIN}$ (NO in step 304), the process proceeds to step 305.

In step 305, the new correction factor $F_{i,NEW}$ is saved as the correction factor $F_i$ for the currently-active application workflow $A_i$. Specifically, the correction factor $F_i$ for the currently-active application workflow $A_i$ is stored within the storage medium 8.

In step 306, the new correction factor $F_{i,NEW}$ is defined to equal to the minimum limit correction factor $F_{i,MIN}$. That is, the new correction factor $F_{i,NEW}$ is set to correspond to the minimum limit correction factor $F_{i,MIN}$.

Subsequently, in step 307, the new correction factor $F_{i,NEW}$ is saved as the correction factor $F_i$ for the currently-active application workflow $A_i$. Specifically, the correction factor $F_i$ for the currently-active application workflow $A_i$ is stored within the storage medium 8.

Then, the process proceeds to the corresponding next step of the method illustrated in FIG. 3 or 4.

Figure 6:
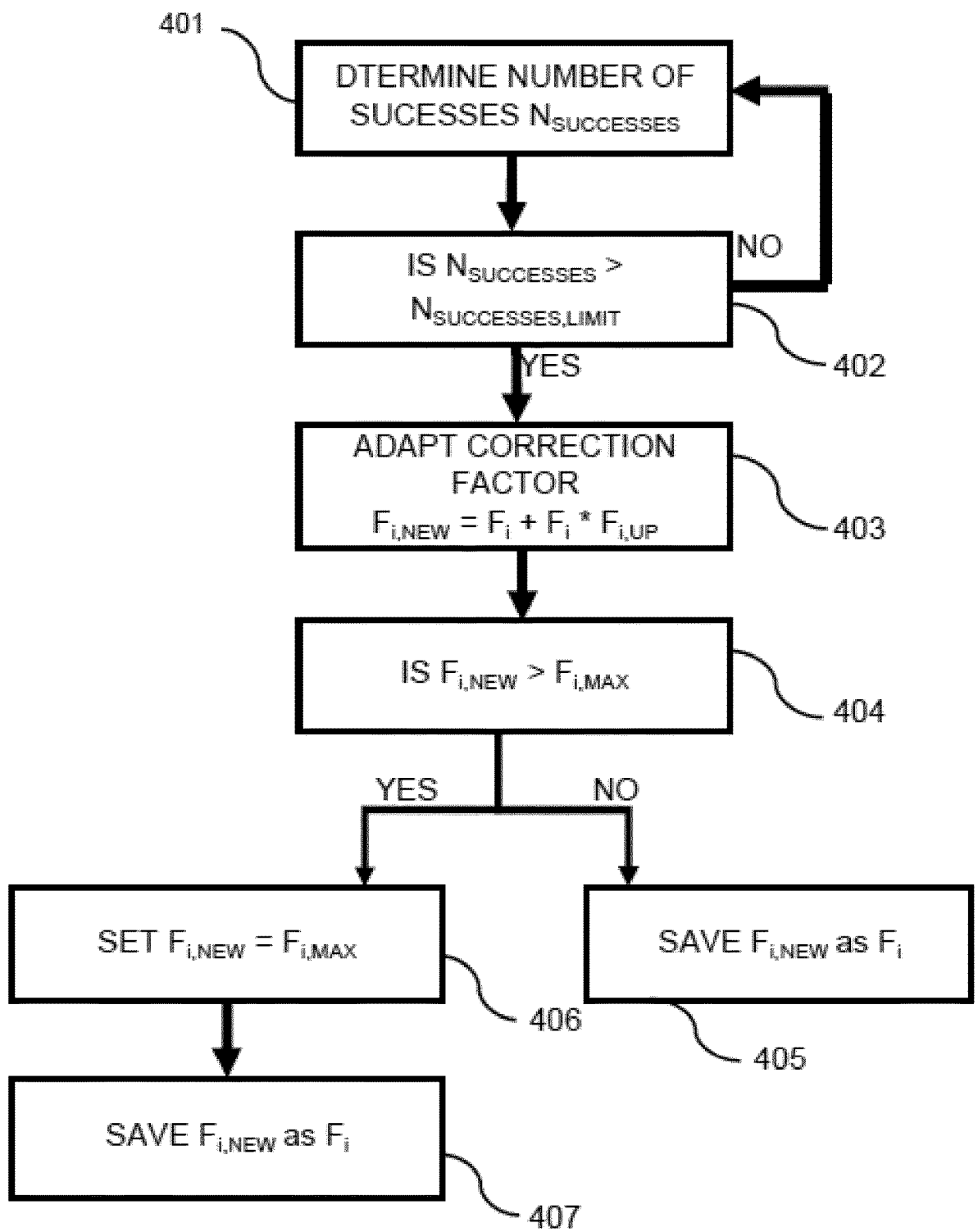
FIG. 6 is a flow chart illustrating a method according to an embodiment of the present invention.

FIG. 6 is a flow chart illustrating a method according to the present invention. Specifically, the method provides an automatic adaption of the correction factor based on the user's pointing device 15 history. In some embodiments, the method illustrated in FIG. 6 is executed in parallel with the method illustrated in FIG. 5. In other embodiments, the method illustrated in FIG. 6 may be executed subsequent to the execution of the method illustrated in FIG. 5 or vice versa.

In step 401 the number of successful operations $N_{SUCCESSES}$ is determined. Specifically, each successful operation in the forward direction made by the user 16 while executing the currently-active application workflow $A_i$ is accumulated. The number of successful operations $N_{SUCCESSES}$ is temporarily stored within the storage medium 8.

In step 402 it is determined, whether the number of successful operations $N_{SUCCESSES}$ exceeds a limit of numbers of successful operations $N_{SUCCESSES,LIMIT}$, or not. If the condition is fulfilled (YES in step 401) the process proceeds to step 403. Otherwise (NO in step 402) the process returns to step 401.

In step 403, the correction factor $F_i$ is adapted in that the a new correction factor $F_{i,NEW}$ is determined based on the current correction factor $F_i$ and a scale up correction factor $F_{i,UP}$. Specifically, the new correction factor $F_{i,NEW}$ is determined by subtracting the product of the current correction factor $F_i$ and the scale up correction factor $F_{i,UP}$ from the current correction factor $F_i$ ($F_{i,NEW}=F_i-F_i*F_{i,UP}$).

In step 404 it is determined whether the new correction factor $F_{i,NEW}$ exceeds a preset maximum limit correction factor $F_{i,MAX}$ which represents a maximum permissible value. In case the new correction factor $F_{i,NEW}$ exceeds the maximum limit correction factor $F_{i,MAX}$ (YES in step 404), the process proceeds to step 406. Otherwise, in case the new correction factor $F_{i,NEW}$ is less than the maximum limit correction factor $F_{i,MAX}$ (NO in step 404), the process proceeds to step 405.

In step 405, the new correction factor $F_{i,NEW}$ is saved as the correction factor $F_i$ for the currently-active application workflow $A_i$. Specifically, the correction factor $F_i$ for the currently-active application workflow $A_i$ is stored within the storage medium 8.

In step 406, the new correction factor $F_{i,NEW}$ is defined to equal to the maximum limit correction factor $F_{i,MAX}$. That is, the new correction factor $F_{i,NEW}$ is set to correspond to the maximum limit correction factor $F_{i,MAX}$.

Subsequently, in step 407, the new correction factor $F_{i,NEW}$ is saved as the correction factor $F_i$ for the currently-active application workflow $A_i$. Specifically, the correction factor $F_i$ for the currently-active application workflow $A_i$ is stored within the storage medium 8.

Then, the process proceeds to the corresponding next step of the method illustrated in FIGS. 3 and 4.

The following commented code provided for illustrative purpose only may be used for the above described method according to one embodiment of the present invention:

```
void AdaptSensitivity(const SPoint& pt)
// SPoint is a structure to hold x and y coordinates
{
  // Increment backwardMovementCounter for movement in reverse direction
  if (pt.x < 0)
  {
    m_backwardMovementCount++;
  }
  else
  {
    // Increment forwardMovementCounter for movement in forward direction
    m_forwardMovement Count++;
  }
  // Decrease Sensitivity Adjustment Factor (Fi) if backwardMovementCount exeeds
    // the maximum allowed direction changes within the
    // autoAdaptScaleDownWindowLimit
  if ((m_backwardMovementCount > m_maxAllowedDirectionChangeCount) && (m_forwardMovementCount < m_autoAdaptScaleDownWindowLimit))
  {
      // Decrease Sensitivity Adjustment Factor (Fi) by the scale down factor
      Fi = Fi - (m_ScaleDownMultiplicationFactor * 0.01) * Fi;
      // Do not decrease Sensitivity Adjustment Factor (Fi)
      // below the minimum permissible value
      if (Fi < minFi);
      {
            Fi = minFi;
      }
      //Reset counters
      m_backwardMovementCount = 0;
      m_forwardMovementCount =0;
  }
  // Increase the Sensitivity Adjustment Factor (Fi),
  // only if the total number of forward movement count reaches
  // autoAdaptScaleUpWindowLimit without any direction changes
  else if (m_forwardMovementCount > m_autoAdaptScaledownWindowLimit)
  {
      // Reset forward counter as soon as a single error is encountered
      if (mbackwardMovementCount != 0)
      (
            m_forwardMovementCount = 0;
      }
      // Reset backward movement counter
      m_backwardMovementCount = 0;
      // Increase Sensitivity Factor (Fi), if there is no direction change till
      // autoAdaptScaleUpWindowLimit
      if (m_forwardMovementCount > m_autoAdaptScaleUpWindowLimit)
      {
            // Increase Sensitivity Factor (Fi) by the scale up factor
            Fi = Fi + (m_ScaleUpMultiplicationFactor * 0,01)* Fi;
            //Don't increase Factor Fi above the maximum permissible value
            if (Fi > maxFi)
```

```
        {
            Fi = maxFi;
        }
        // Reset counters
        m_backwardMovementCount = 0;
        m_forwardMovementCount = 0;
      }
    }
}
```

FIG. 7 shows a schematically flow chart illustrating a further embodiment of the present invention. In the embodiment illustrated in FIG. 7, the image evaluation device 1 is defined to be an ultrasound system and the pointing device 15 is defined to be a touchpad.

First, in step 501 a user enters a specific application (i.e. one of the plurality of application workflows A1, A2, . . . , An) and performs a move operation on the touchpad.

In step 502 the delta move points Δx, Δy are send to the active application (i.e. the currently-active application workflow).

In step 503 it is determined, whether the active application is configured to control touchpad move points, or not. In case the result of step 503 is yes (YES in step 503), the process proceeds to step 505. Otherwise (NO in step 503), the process proceeds to step 504.

In step 504 the delta move points received from the touchpad driver are used for calculating a new cursor position. Subsequently, the process proceeds to step 507.

In step 505 a scaling factor (i.e. the correction factor) is applied to the delta move points Δx, Δy received from the touchpad driver for calculating new cursor position. During the step 505 the scaling factor is automatically adapted in step 506. In other words, in step 506 the touchpad sensitivity scaling factor is auto adapted and subsequently the adapted scaling factor is saved. Subsequently, the new scaling factor is inputted to step 505.

Then the process moves on to step 507. In step 507 the final movement of the cursor 14 is performed.

While the invention has been illustrated and described in detail in the drawings and foregoing description, such illustration and description are to be considered illustrative or exemplary and not descriptive; the invention is not limited to the disclosed embodiments.

The invention claimed is:

1. A method for adapting sensitivity of a pointing device connected to a processor configured to execute a plurality of application workflows, and to a display configured to display a cursor, wherein the method comprises the steps of:
receiving a default sensitivity (S) of the pointing device;
determining one of the plurality of application workflows which is to be executed, said application workflow being the currently-active application workflow ($A_i$);
receiving or determining a target sensitivity ($S_i$) for the currently-active application workflow ($A_i$);
receiving or determining a correction factor ($F_i$) for the currently-active application workflow based on the target sensitivity ($S_i$) for the currently-active application workflow and the default sensitivity (S);
receiving a current position of the cursor;
detecting delta coordinates inputted by an operation made by the user on the pointing device in order to move the cursor on the display during execution of the currently-active application workflow; and
computing, in response to the operation of the user on the pointing device, a new position of the cursor on the display based on the current position of the cursor, the delta coordinates and the correction factor ($F_i$) for the currently-active application workflow ($A_i$).

2. The method for adapting sensitivity of a pointing device according to claim 1, wherein the correction factor ($F_i$) for the currently-active application workflow is a ratio of the target sensitivity ($S_i$) for the currently-active application workflow and the default sensitivity (S).

3. The method for adapting sensitivity of a pointing device according to claim 1, wherein the pointing device is a touchpad configured to receive a touch gesture based on the user's operation on the touchpad.

4. The method for adapting sensitivity of a pointing device according to claim 1, wherein for each application workflow of the plurality of application workflows there is defined a corresponding target sensitivity.

5. The method for adapting sensitivity of a pointing device according to claim 1, wherein the correction factor ($F_i$) for the currently-active application workflow ($A_i$) is automatically adapted based on the user's pointing device navigation history for said application workflow ($A_i$), preferably based on the user s last use of the pointing device for said application workflow ($A_i$).

6. The method for adapting sensitivity of a pointing device according to claim 1, wherein the method comprises the steps of:
determining a number of erroneous operations ($N_{ERROR}$) made by the user on the pointing device, wherein an operation is defined to be erroneous when the user causes the cursor to move in a reverse direction in order to undo a previously made move operation of the cursor;
determining a number of successful operations ($N_{SUCCESSES}$) made by the user on the pointing device, wherein an operation is defined to be successful when the user causes the cursor to move in a forward direction in order to perform a further forward move operation of the cursor; and
adapting the correction factor for the currently-active application workflow based on the determined number of erroneous operations ($N_{ERROR}$) and successful operations ($N_{SUCESSES}$).

7. The method for adapting sensitivity of a pointing device according to claim 6, wherein
the correction factor ($F_i$) for the currently-active application workflow ($A_i$) is adapted by subtracting a scale down factor ($F_{i,down}$) multiplied by the correction factor ($F_i$) from the correction factor ($F_i$), if the number of erroneous operations ($N_{ERROR}$) exceeds a predefined first threshold value ($N_{ERROR,LIMIT}$) and if the movement of the cursor in the forward direction due to the operation of the user is within a predefined window limit of move points, or the correction factor ($F_i$) for the currently-active application workflow ($A_i$) is adapted by adding a scale up factor ($F_{i,up}$) multiplied by the correction factor ($F_i$) to the correction factor ($F_i$), if the number of successful operations ($N_{SUCESSES}$) exceeds a predefined second threshold value ($N_{SUCESSES,LIMIT}$).

8. The method for adapting sensitivity of a pointing device according to claim 6, wherein
the correction factor ($F_i$) for the currently-active application workflow ($A_i$) is adapted by subtracting a scale down factor ($F_{i,down}$) multiplied by the correction factor ($F_i$) from the correction factor ($F_i$), if the number of erroneous operations ($N_{ERROR}$) exceeds a predefined first threshold value ($N_{ERROR,LIMIT}$) within a predefined period of time, or
the correction factor ($F_i$) for the currently-active application workflow ($A_i$) is adapted by adding a scale up factor ($F_{i,up}$) multiplied by the correction factor ($F_i$) to the correction factor ($F_i$), if the number of successful operations ($N_{SUCCESSES}$) exceeds a predefined second threshold value ($N_{SUCESSES,LIMIT}$).

9. The method for adapting sensitivity of a pointing device according to claim 7, wherein for each application workflow of the plurality of application workflows there is defined a corresponding predefined first ($N_{SUCESSES,LIMIT}$) and/or second threshold value ($N_{SUCESSES,LIMIT}$).

10. The method for adapting sensitivity of a pointing device according to claim 1,
wherein the target sensitivity for at least one application workflow of the plurality of application workflows may be adapted by the user via an user interface.

11. The method for adapting sensitivity of a pointing device according to claim 5, wherein, when the currently-active application workflow ($A_i$) is terminated, the adapted correction factor ($F_i$) is saved within a storage connected to the processor.

12. The method for adapting sensitivity of a pointing device according to claim 1, wherein the method comprises the steps of:
setting the correction factor for the currently-active application workflow ($A_i$) to a predefined maximum correction factor ($F_{i,max}$) if said correction factor ($F_i$) exceeds a predefined maximum correction factor ($F_{i,max}$); or
setting the correction factor for the currently-active application workflow to a predefined minimum correction factor ($F_{i,min}$) if said correction factor ($F_i$) falls below a predefined minimum correction factor ($F_{i,min}$).

13. A non-transitory computer-readable medium comprising program code instructions, which, when executed by a processor connected to a display, enables the processor to carry out the method according to claim 1.

14. An image evaluation device configured to execute a plurality of application workflows and to perform the method of claim 1, comprising:
a display configured to display an image for evaluation and a cursor;
a pointing device configured to detect delta coordinates of an operation made by a user on the pointing device in order to perform a move operation of the cursor on the display;
a processor configured to receive a default sensitivity (S) of the pointing device, to determine one of the plurality of application workflows which is to be executed, said application workflow being the currently-active application workflow, to receive or determine a target sensitivity ($S_i$) for the currently-active application workflow ($A_i$), to receive or determine a correction factor ($F_i$) for the currently-active application workflow based on the target sensitivity ($S_i$) for the currently-active application workflow and the default sensitivity (S) and to compute, in response to the operation of the user on the pointing device, a new position ($x_{NEW}$, $y_{NEW}$) of the cursor on the display based on a current position of the cursor, the delta coordinates, and the correction factor ($F_i$) for the currently-active application workflow ($A_i$).

15. The image evaluation device according to claim 14, wherein the correction factor for the currently-active application workflow is a ratio of the target sensitivity ($S_i$) for the currently-active application workflow and the default sensitivity (S).

16. The method of claim 1, wherein the display is a graphical display comprising at least one of a screen, monitor, touch-screen, projected image.

17. The method of claim 1, wherein the cursor is at least one of a marker, a measurement cursor, an annotation or an arrow.

18. The method of claim 1, wherein the pointing device is at least one of a marker, a measurement cursor, an annotation or an arrow.

19. The method of claim 1, wherein the application workflow is at least one of:
a software program;
an application software including at least one of text and image processing applications, an email application, and a browser;
a clinical application;
an operating system;
an image evaluation software program, and
a workflow used to control a medical imaging device or a medical image evaluation device.

* * * * *